(12) United States Patent
Kawahara et al.

(10) Patent No.: US 11,311,423 B2
(45) Date of Patent: *Apr. 26, 2022

(54) FACIAL PATCH

(71) Applicant: Nichiban Co., Ltd., Tokyo (JP)

(72) Inventors: Koji Kawahara, Tokyo (JP); Takao Hiraoka, Tokyo (JP); Mariko Tanaka, Tokyo (JP); Chihiro Kenmochi, Tokyo (JP)

(73) Assignee: NICHIBAN CO., LTD., Tokyo (JP)

( * ) Notice: Subject to any disclaimer, the term of this patent is extended or adjusted under 35 U.S.C. 154(b) by 1337 days.

This patent is subject to a terminal disclaimer.

(21) Appl. No.: 14/653,097

(22) PCT Filed: Dec. 19, 2012

(86) PCT No.: PCT/JP2012/082908
§ 371 (c)(1),
(2) Date: Jun. 17, 2015

(87) PCT Pub. No.: WO2014/097422
PCT Pub. Date: Jun. 26, 2014

(65) Prior Publication Data
US 2015/0320606 A1    Nov. 12, 2015

(51) Int. Cl.
*A61F 13/12* (2006.01)
*A61F 13/02* (2006.01)
*A45D 44/22* (2006.01)
*B32B 7/12* (2006.01)
*B32B 7/06* (2019.01)
*B32B 27/08* (2006.01)
*B32B 27/32* (2006.01)
*B32B 27/36* (2006.01)

(52) U.S. Cl.
CPC .......... *A61F 13/122* (2013.01); *A45D 44/22* (2013.01); *A61F 13/0253* (2013.01); *A61F 13/0283* (2013.01); *A61F 13/12* (2013.01); *B32B 7/06* (2013.01); *B32B 7/12* (2013.01); *B32B 27/08* (2013.01); *B32B 27/32* (2013.01); *B32B 27/36* (2013.01); *B32B 2255/10* (2013.01); *B32B 2255/26* (2013.01); *B32B 2307/51* (2013.01); *B32B 2556/00* (2013.01); *Y10T 428/1452* (2015.01)

(58) Field of Classification Search
CPC .............. B32B 7/06; B32B 7/12; B32B 27/08
See application file for complete search history.

(56) References Cited

U.S. PATENT DOCUMENTS

| | | | | |
|---|---|---|---|---|
| 3,345,248 A * | 10/1967 | Pounds | .................... | B32B 27/00 156/60 |
| 5,221,534 A * | 6/1993 | DesLauriers | .......... | A61K 8/042 424/401 |
| 6,512,158 B1 * | 1/2003 | Dobos | .................... | A61F 15/004 602/3 |
| 6,914,169 B1 | 7/2005 | Oota et al. | | |
| 6,974,588 B1 * | 12/2005 | Miranda | .............. | A61K 9/7061 424/448 |
| 9,211,397 B2 * | 12/2015 | Ogawa | .................... | A61L 15/58 |
| 2004/0127531 A1 * | 7/2004 | Lu | ........................ | A61K 9/7007 514/378 |
| 2005/0260255 A1 * | 11/2005 | Terahara | .............. | A61K 9/7061 424/449 |
| 2009/0022778 A1 | 1/2009 | Yamaji et al. | | |
| 2010/0217171 A1 | 8/2010 | Fukano et al. | | |
| 2013/0152944 A1 * | 6/2013 | Okada | .................... | A45D 44/12 128/846 |
| 2014/0171886 A1 * | 6/2014 | Ogawa | .................... | A61L 15/58 604/307 |

FOREIGN PATENT DOCUMENTS

| | | | |
|---|---|---|---|
| EP | 1210937 A2 | 6/2002 | |
| JP | 5-017346 A | 1/1993 | |
| JP | 2000-513347 A | 10/2000 | |
| JP | 2001-328935 A | 11/2001 | |
| JP | 2004121828 A | * | 4/2004 |
| JP | 2005-154414 A | 6/2005 | |
| JP | 2006-008593 A | 1/2006 | |

(Continued)

OTHER PUBLICATIONS

LDPE elastic modulus, http://www.substech.com/dokuwiki/doku.php?id=thermoplastic_low_density_polyethylen . . . Feb. 12, 2019 (Year: 2019).*
Derwent Abstract of JP 2004-121828. See above for inventor (Year: 2004).*
Low Density Polyethylene Properties, MatWeb database. Jun. 17, 2020 (Year: 2020).*

* cited by examiner

*Primary Examiner* — Anish P Desai
(74) *Attorney, Agent, or Firm* — Porter Wright Morris & Arthur LLP

(57) ABSTRACT

Provided is a facial patch including a support, a pressure-sensitive adhesive layer, and a release layer in this order, in which (a) the pressure-sensitive adhesive layer satisfies the following conditions (a-1) to (a-3): (a-1) the pressure-sensitive adhesive layer contains a styrene-isoprene-styrene block copolymer, a tackifier resin, and a softening agent; (a-2) the ratio (mass ratio) of the styrene-isoprene-styrene block copolymer and the tackifier resin is 1:2 to 1:4; and (a-3) the content of the softening agent is 40% to 60% by mass; and (b) the support has elastic moduli with a Young's modulus of 0.01 GPa to 0.5 GPa, and also provided is a method for producing the facial patch, the method including a step of forming a pressure-sensitive adhesive layer on the upper surface of the release layer.

13 Claims, No Drawings

(56) References Cited

FOREIGN PATENT DOCUMENTS

| JP | 2007-215578 A | 8/2007 |
|---|---|---|
| WO | 2006/092829 A1 | 9/2006 |
| WO | 2009/041122 A1 | 4/2009 |

FACIAL PATCH

TECHNICAL FIELD

The present invention relates to a facial patch applicable onto a face that oversupplies sebum.

BACKGROUND ART

An adhesive patch that is used by applying onto the skin has a layered structure including a support and a pressure-sensitive adhesive layer provided on at least one surface of the support. Furthermore, many of adhesive patches have a layered structure in which a release layer is disposed in order to protect the surface of the pressure-sensitive adhesive layer, or for example, in a case in which the support is extremely thin, a carrier layer such as a carrier film is provided on the support.

An adhesive patch is removed after being applied onto the skin, and thereafter, in many case, a fresh patch is applied. Therefore, it is required that the adhesive patch do not fall off from the skin for an intended time period, can be removed easily and neatly, and do not cause strong irritation to the skin. Furthermore, in a case in which the patch is applied onto a portion where the skin is exposed in the daily life, such as the face, it is also required that the applied portions do not remain conspicuous.

That is, an adhesive patch is required to have appropriate adhesive force. If the adhesive force is too weak, the patch may be easily removed from the skin surface, or may not adhere along a skin surface having minute irregularities such as skin furrows. If the adhesive force is too strong, skin eruption may occur, or removal of the patch after use may become difficult.

The face is a portion where sebum is overly secreted, compared with the arms, shoulders and the like. In a case in which an adhesive patch is applied onto the face that overly secretes sebum, as the adhesive of the pressure-sensitive adhesive layer absorbs the sebum secreted from the skin of the face, the cohesive force of the pressure-sensitive adhesive is decreased, and there is a risk that the patch may easily peel off. Thus, it has been thought that in order to prevent the adhesive patch from peeling off even if the patch absorbs a large amount of sebum, it is necessary to make the thickness of the pressure-sensitive adhesive layer sufficiently large.

The so-called T-zone area of the face including the forehead, the nose and the like is a portion where the amount of secretion of sebum is particularly large, and is also a portion where acne is prone to develop. It is necessary for a portion where acne has developed to be maintained as clean as possible. When foundation or the like is applied directly on the skin after cleansing of the face, there is a risk that reddening of the skin at the portion with acne may be aggravated, or suppuration may occur. If the thickness of the pressure-sensitive adhesive layer is made small, it is likely to have difficulties in obtaining appropriate adhesive force.

Therefore, there has been a demand for a facial patch that can be applied over a long period of time onto the skin of the face, which is a portion with a large amount of secretion of sebum, and that has less residual adhesive and is less irritating to the skin. In addition, there has been a demand for a patch for which the state of adhesion does not remain conspicuous.

For example, Patent Literature 1 discloses a nose patch which exhibits satisfactory adhesiveness over a long period of time, causes no skin irritation, and does not cause pain at the time of removal, and which includes a pressure-sensitive adhesive layer formed from a pressure-sensitive adhesive composition containing a pressure-sensitive adhesive, a fragrance and a fatty acid ester on one surface of a support. Patent Literature 2 discloses a pressure-sensitive adhesive article in which a patterned pressure-sensitive adhesive layer is disposed on an oil-absorbent base material (corresponding to a support). Patent Literature 3 discloses a patch type device containing an anti-acne (that is, acne) formulation containing at least two kinds of effective components. Furthermore, Patent Literature 4 discloses a thin adhesive patch to be applied onto human face or the like, the patch having a support and a pressure-sensitive adhesive layer that are both adhered along a surface of the skin having minute irregularities.

In regard to the adhesive patches disclosed in these literatures, examples of the pressure-sensitive adhesive of the pressure-sensitive adhesive layer include a rubber-based pressure-sensitive adhesive, an acrylic pressure-sensitive adhesive, and a silicone-based pressure-sensitive adhesive. Furthermore, examples of the support include fabrics such as a nonwoven fabric, a woven fabric, and a knitted fabric; various papers; and plastic films of polyesters, polyurethanes, polyethylene, and polypropylene.

Furthermore, Patent Literature 5 discloses a medical patch in which a pressure-sensitive adhesive layer containing a pressure-sensitive adhesive base containing a paraffin-based hydrocarbon and/or a naphthene-based hydrocarbon, an alicyclic hydrocarbon resin, and a styrene-isoprene-styrene block copolymer is provided on one surface of a support. Examples of the support include synthetic resin films of polyester, polyethylene, polyvinyl chloride, polyvinylidene chloride, a polyethylene-vinyl acetate copolymer and polyurethane; a nonwoven fabric, a fabric, and an aluminum foil, and it is specifically disclosed that a soft vinyl chloride film having a thickness of 135 μm is used. Furthermore, Patent Literature 6 discloses a patch for external use in which a pressure-sensitive adhesive layer containing a styrene-isoprene-styrene block copolymer, a tackifier resin, and a softening agent as essential components and formed by incorporating flurbiprofen therein as an active ingredient is laminated on a support. Examples of the support include a nonwoven fabric and a woven fabric.

However, it still cannot be said that conventional adhesive patches are sufficiently effective as facial patches for the face that overly secretes sebum. There is a demand for a combination of a support and a pressure-sensitive adhesive layer that can provide a facial patch which can be applied over a long period of time onto the skin of the face that overly secretes sebum, which has less residual adhesive and is less irritating to the skin, and for which the state of adhesion does not remain conspicuous.

CITATION LIST

Patent Literature

Patent Literature 1: JP 2006-8593 A
Patent Literature 2: JP 2007-215578 A
Patent Literature 3: JP 2000-513347 W
Patent Literature 4: WO 2009/041122
Patent Literature 5: JP 5-17346 A
Patent Literature 6: WO 2006/092829

SUMMARY OF INVENTION

Technical Problem

An object of the present invention is to provide a facial patch which can be applied over a long period of time onto the skin of the face that overly secretes sebum, and which has less residual adhesive and is less irritating to the skin.

Solution to Problem

The inventors of the present invention conducted a thorough investigation in order to solve the problems described above, and as a result, the inventors found that the above-described problems can be solved by employing an optimal combination of a pressure-sensitive adhesive layer and a support.

That is, the present invention provides a facial patch including a support, a pressure-sensitive adhesive layer, and a release layer in this order, wherein
(a) the pressure-sensitive adhesive layer satisfies the following conditions (a-1) to (a-3):
(a-1) the pressure-sensitive adhesive layer contains a styrene-isoprene-styrene block copolymer, a tackifier resin, and a softening agent;
(a-2) the ratio (mass ratio) of the styrene-isoprene-styrene block copolymer and the tackifier resin is 1:2 to 1:4; and
(a-3) the content of the softening agent is 40% to 60% by mass; and
(b) the support has elastic moduli with a Young's modulus of 0.01 GPa to 0.5 GPa.

Furthermore, according to the present invention, facial patches of the following items (1) to (11) are provided as embodiments.
(1) The facial patch, wherein the styrene-isoprene-styrene block copolymer includes a styrene-isoprene-styrene block copolymer having a percentage content of styrene of 20% by mass or more.
(2) The facial patch, wherein the styrene-isoprene-styrene block copolymer includes a styrene-isoprene-styrene block copolymer having a percentage content of styrene of 15% by mass or more and an amount of diblocks of 30% by mass or less.
(3) The facial patch, wherein the pressure-sensitive adhesive layer further satisfies the following conditions (a-2') and (a-3'):
(a-2') the ratio (mass ratio) of the styrene-isoprene-styrene block copolymer and the tackifier resin is 1:2.4 to 1:3.5; and
(a-3') the content of the softening agent is 40% to 55% by mass.
(4) The facial patch, wherein the tackifier resin is a terpene resin.
(5) The facial patch, wherein the softening agent is a liquid at room temperature.
(6) The facial patch, wherein the softening agent is liquid paraffin.
(7) The facial patch, wherein the pressure-sensitive adhesive layer contains a drug.
(8) The facial patch, wherein the support is a polyethylene film having a thickness of 1 μm to 80 μm.
(9) The facial patch, including a carrier film on a surface of the support on the opposite side of the pressure-sensitive adhesive layer.
(10) The facial patch, wherein the carrier film is a polyester film.
(11) The facial patch, wherein the carrier film is provided with matt finish to a surface on the support side.

Further, the present invention provides a method for producing the facial patch, the method including forming a pressure-sensitive adhesive layer on the upper surface of the release layer.

Advantageous Effects of Invention

According to the present invention, an effect that can provide a facial patch which can be applied over a long period of time onto the skin of the face that overly secretes sebum and which has less residual adhesive and is less irritating to the skin, is obtained by using the facial patch described above including a support, a pressure-sensitive adhesive layer, and a release layer in this order, characterized in that:
(a) the pressure-sensitive adhesive layer satisfies the following conditions (a-1) to (a-3):
(a-1) the pressure-sensitive adhesive layer contains a styrene-isoprene-styrene block copolymer, a tackifier resin, and a softening agent;
(a-2) the ratio (mass ratio) of the styrene-isoprene-styrene block copolymer and the tackifier resin is 1:2 to 1:4; and
(a-3) the content of the softening agent is 40% to 60% by mass, and
(b) the support has elastic moduli with a Young's modulus of 0.01 GPa to 0.5 GPa.

Furthermore, according to the present invention, there is obtained an effect that the facial patch described above can be produced easily.

DESCRIPTION OF EMBODIMENTS

The facial patch of the present invention is a facial patch including a support, a pressure-sensitive adhesive layer, and a release layer in this order, and is characterized by the combination of the support and the pressure-sensitive adhesive layer.

1. Support

The facial patch of the present invention includes a support having elastic moduli with a Young's modulus of 0.01 GPa to 0.5 GPa as the support.

As the facial patch of the present invention includes a support having elastic moduli with a Young's modulus of 0.01 GPa to 0.5 GPa as the support, the facial patch can adhere to the skin of the face and can have flexibility to the extent that can follow the movement of the skin. As a result, a facial patch which can be applied over a long period of time onto the skin of the face that overly secretes sebum and which has less residual adhesive and is less irritating to the skin, can be provided. Furthermore, as will be described below, since a substantially highly transparent plastic film is used as the support in many cases, there can be provided a facial patch for which the state of adhesion does not remain conspicuous. If the Young's modulus of the support is too small, the strength of the facial patch is insufficient, and therefore, the facial patch may be torn off in a case in which the facial patch is applied onto the face or the facial patch is removed after having been applied for a necessary time period. If the Young's modulus of the support is too large, the facial patch cannot adhere to the skin of the face or cannot follow the movement of the skin, and the facial patch may not be applied over a long period of time.

The support that is provided to the facial patch of the present invention is not particularly limited as long as the Young's modulus of the support is 0.01 GPa to 0.5 GPa, preferably 0.03 GPa to 0.48 GPa, and more preferably 0.05 GPa to 0.45 GPa; however, in many cases, it is appropriate to use a plastic film having elastic moduli with a Young's modulus of 0.01 GPa to 0.5 GPa. The Young's modulus of a plastic film is measured in conformity to ASTM-D-882, and the support provided to the facial patch of the present invention has elastic moduli with a Young's modulus of 0.01 GPa to 0.5 GPa in both the MD direction of the film (direction of extrusion at the time of film molding) and the TD direction (a direction perpendicular to the direction of extrusion at the time of film molding).

In general, examples of the plastic that serves as the material for the plastic film used as a support of the adhesive patch include synthetic resins including polyolefins such as polyethylene and polypropylene; polyesters such as polyethylene terephthalate, polybutylene terephthalate, and polyethylene naphthalate; polystyrene; polyamides such as Nylon 6, Nylon 66, and MXD6; polyvinyl alcohol; an ethylene-vinyl acetate copolymer; polyurethanes such as an acrylic polyurethane, a polyester-based polyurethane, and a polyether-based polyurethane; synthetic rubbers such as a styrene-isoprene-styrene copolymer, a styrene-butadiene-styrene copolymer, a styrene-ethylene-propylene-styrene copolymer, and a styrene-butadiene rubber. A plastic film formed by molding a synthetic resin composition obtained by incorporating various organic additives (may be resins) or inorganic additives to these synthetic resins, singly or as a mixture, or a laminate of such plastic films, may be employed. Regarding these plastic films, an unstretched film, a uniaxially stretched film, or a biaxially stretched film may be selected.

The plastic film having elastic moduli with a Young's modulus of 0.01 GPa. to 0.5 GPa, which is suitable for the use as a support of the facial patch of the invention, can be produced by selecting the composition of the material or selecting the molding conditions so as to form a plastic film having elastic moduli with the necessary Young's modulus using a plastic such as one of the synthetic resins described above, as a main material.

Specifically, from the viewpoint of the ease of adjustment of the Young's modulus or the like, polyolefins such as polyethylene (low density polyethylene, high density polyethylene, linear low density polyethylene, or the like), and polypropylene; polyurethanes; polyamides such as Nylon 6 can be preferably used as the material, and particularly a polyethylene film, an unstretched polypropylene film, an unstretched polyamide film, and the like are suitable. In regard to a polyester film and the like, if polyester is used alone, the film may not have elastic moduli with a Young's modulus of 0.01 GPa to 0.5 GPa; however, the polyester film may be produced to have elastic moduli with a Young's modulus of 0.01 GPa to 0.5 GPa by incorporating a resin blend or additives.

There are no particular limitations on the characteristics such as molecular weight, melting point, glass transition temperature, and melt viscosity of the synthetic resin preferable as the material that forms the support of the facial patch of the present invention, and the characteristics may be selected from the ranges such that the resulting plastic film can have the elastic moduli with a Young's modulus of 0.01 GPa to 0.5 GPa as required from the support.

[Thickness of Support]

The thickness of the support that is included in the facial patch of the present invention is not particularly limited; however, the thickness is usually in the range of 1 μm to 80 μm, preferably in the range of 3 μm to 70 μm, and more preferably in the range of 5 μm to 60 μm. Therefore, the most preferred support is a polyethylene film having a thickness of 5 μm to 60 μm. From the viewpoint of making the facial patch inconspicuous during application and mitigating the sense of discomfort, the thickness of the support can also be decreased to the range of 2 μm to 20 μm, and preferably to 5 μm to 20 μm. If the thickness of the support is too small, the strength of the support becomes insufficient so that the support may be broken when the facial patch is applied onto the face or the facial patch is peeled off from the face, and the production of the support may be difficult. If the thickness of the support is too large, the thickness of the facial patch is increased, and as a result, it is difficult for the facial patch to adhere along the skin surface of a face having minute irregularities such as skin furrows, the state of attachment becomes conspicuous, the sense of discomfort is likely to increase, and the pain at the time of removal also increases. The thickness of the support is measured using a dial thickness gauge. Meanwhile, the method for measuring the thicknesses of other layers of the facial patch is also carried out in the same manner.

[Additives]

In the synthetic resin composition for forming a plastic film that serves as a support, various organic additives or inorganic additives, such as colorants including pigments and dyes, stabilizers, ultraviolet absorbers, and lubricating agents, can be incorporated as desired. Regarding the contents of these additives, the optimal ranges may be selected depending on the kind of the additives; however, in many cases, the content of an additive is usually set to the range of 0.001 parts by mass to 30 parts by mass, preferably 0.01 parts by mass to 25 parts by mass, and more preferably 0.1 parts by mass to 20 parts by mass, relative to 100 parts by mass of the synthetic resin that constitutes fee plastic film.

[Matt Finish]

In order to improve the feel of touch, sliding properties, external appearance and the like of the facial patch when the facial patch is applied onto the skin surface of the face, it may be preferable to form minute irregularities on the back surface of the support that constitutes the facial patch (meaning a surface located on the opposite side of the pressure-sensitive adhesive layer in the support). That is, a patch in which the surface on the opposite side of the pressure-sensitive adhesive layer in the support is matt finished, can be provided. By performing matt finish, the dynamic friction coefficient of the support surface can be decreased to a value less than 1.0. Meanwhile, as will be described below, when a facial patch is produced, if minute irregularities are formed on the surface of a carrier film by matte processing, and a support is formed on this surface of minute irregularities, the minute irregularities can be transferred to the front surface (back surface) of the support, which is a plastic film.

Furthermore, the support may be subjected to a surface treatment such as a sand blast treatment or a corona treatment on one surface or on both surfaces, for the purpose of enhancing the anchoring properties against the pressure-sensitive adhesive, and the like. Furthermore, in order to make it easier to remove the adhesive patch from a cloth material, irregularities may be provided on one surface or on both surfaces of the support by a method other than sandblasting.

2. Pressure-sensitive Adhesive Layer

The facial patch of the present invention is characterized in that the pressure-sensitive adhesive layer has the following features (a-1) to (a-3):

(a-1) the pressure-sensitive adhesive layer contains a styrene-isoprene-styrene block copolymer, a tackifier resin, and a softening agent;

(a-2) the ratio (mass ratio) of the styrene-isoprene-styrene block copolymer and the tackifier resin is 1:2 to 1:4; and (a-3) the content of the softening agent is 40% to 60% by mass.

[Pressure-sensitive Adhesive]

In general, the pressure-sensitive adhesive layer of an adhesive patch is formed from a pressure-sensitive adhesive which exhibits pressure-sensitive adhesiveness at normal temperature, and examples of a pressure-sensitive adhesive having low skin irritancy that may be used include acrylic pressure-sensitive adhesives, natural rubber-based pressure-sensitive adhesives, synthetic rubber-based pressure-sensitive adhesives, silicone-based pressure-sensitive adhesives, vinyl ester-based pressure-sensitive adhesives, vinyl ether-based pressure-sensitive adhesives, and urethane-based pressure-sensitive adhesives. The pressure-sensitive adhesive that forms the pressure-sensitive adhesive layer included in the facial patch of the present invention belong to the class of synthetic rubber-based pressure-sensitive adhesives.

The facial patch of the present invention is further a synthetic rubber-based pressure-sensitive adhesive containing a styrene-isoprene-styrene block copolymer as a synthetic rubber. The facial patch of the present invention is less irritating to the skin, adheres along the irregularities of the skin surface so that the applied portion is inconspicuous, and the pressure-sensitive characteristics are easily controlled so that the application is maintained over a long period of time even at a portion where sebum is overly secreted. Therefore, the pressure-sensitive adhesive layer has a characteristic composition that satisfies the following conditions (a-1) to (a-3):

(a-1) the pressure-sensitive adhesive layer contains a styrene-isoprene-styrene block copolymer, a tackifier resin, and a softening agent;

(a-2) the ratio (mass ratio) of the styrene-isoprene-styrene block copolymer and the tackifier resin is 1:2 to 1:4; and (a-3) the content of the softening agent is 40% to 60% by mass.

[Styrene-isoprene-styrene Block Copolymer]

In regard to the facial patch of the present invention, the pressure-sensitive adhesive layer contains a styrene-isoprene-styrene block copolymer. The styrene-isoprene-styrene block copolymer is not particularly limited as long as it is a styrene-isoprene-styrene block copolymer that is used in synthetic rubber-based pressure-sensitive adhesives for adhesive patches, for example, a styrene-isoprene-styrene block copolymer having a percentage content of styrene of about 5% by mass or more. However, it is preferable that the styrene-isoprene-styrene block copolymer includes a styrene-isoprene-styrene block copolymer having a percentage content of styrene of about 20% by mass or more, and it is preferable that the styrene-isoprene-styrene block copolymer includes a styrene-isoprene-styrene block copolymer having a percentage content of styrene of 15% by mass or more and an amount of diblocks of 30% by mass or less. The percentage content of styrene in the styrene-isoprene-styrene block copolymer is more preferably 17% by mass or more, and even more preferably 20% by mass or more. There is no particular upper limit in the percentage content of styrene; however, from the viewpoint of viscoelasticity of the pressure-sensitive adhesive, the upper limit is usually 30% by mass. The amount of diblocks in the styrene-isoprene-styrene block copolymer is more preferably 25% by mass or less, and even more preferably 20% by mass or less. There is no particular lower limit in the amount of diblocks; however, in view of synthesis, the lower limit is usually 5% by mass. If the percentage content of styrene is too small or the amount of diblocks is too large in the styrene-isoprene-styrene block copolymer, when the facial patch is removed, residual adhesive may remain, or skin irritation may become severe, causing reddening of the skin. A styrene-isoprene-styrene block copolymer having a percentage content of styrene of 20% by mass or more, or a styrene-isoprene-styrene block copolymer having a percentage content of styrene of 15% by mass or more and an amount of diblocks of 30% by mass or less (hereinafter, the two copolymers may be collectively called "a high-styrene content styrene-isoprene-styrene block copolymer"), which are both preferably used, may be produced by polymerizing the monomers styrene and isoprene while adjusting the polymerization conditions, or a commercially available product may be selected and used. Known examples of the commercially available product include JSR SIS5002 (percentage content of styrene: 22% by mass, amount of diblocks: 15% by mass) and JSR SIS5000 (percentage content of styrene; 14% by mass, amount of diblocks: 26% by mass) manufactured by JSR Corp. The styrene-isoprene-styrene block copolymer may be used singly or as mixtures of various kinds.

Regarding the styrene-isoprene-styrene block copolymer incorporated in the pressure-sensitive adhesive layer of the facial patch of the present invention, only the high-styrene content styrene-isoprene-isoprene block copolymer described above may be used, or other styrene-isoprene-styrene block copolymers may be used together on condition that the pressure-sensitive adhesive layer contains the high-styrene content styrene-isoprene-styrene block copolymer at a proportion of 50% by mass or more, more preferably 70% by mass or more, and even more preferably 90% by mass, of styrene-isoprene-styrene block copolymers.

The percentage content of styrene in the styrene-isoprene-styrene block copolymer can be measured by infrared spectroscopy, and the amount of diblocks can be measured by a gel permeation chromatography (GPC) method.

The weight average molecular weight of the styrene-isoprene-styrene block copolymer is usually in the range of 50,000 to 1,500,000, preferably 80,000 to 1,000,000, and more preferably 100,000 to 400,000. When the weight average molecular weight of the styrene-isoprene-styrene block copolymer is adjusted to the range described above, a balance can be achieved between cohesiveness, pressure-sensitive adhesive force, miscibility with other components, affinity with other components, and the like of the styrene-isoprene-styrene block copolymer. The weight average molecular weight of the styrene-isoprene-styrene block copolymer is a value determined by a GPC method and calculated relative to polystyrene standards.

[Tackifier Resin]

The pressure-sensitive adhesive layer of the facial patch of the present invention contains a styrene-isoprene-styrene block copolymer, a tackifier resin, and a softening agent, and the ratio (mass ratio) of the styrene-isoprene-styrene block copolymer and the tackifier resin is 1:2 to 1:4. That is, as the pressure-sensitive adhesive layer of the facial patch of the present invention contains a tackifier resin in an amount of 2 to 4 times (mass ratio) the amount of the styrene-isoprene-styrene block copolymer, a facial patch which can be applied over a long period of time onto the skin of the face that overly secretes sebum and which has less residual adhesive and is less irritating to the skin, is provided. The ratio (mass ratio) of the styrene-isoprene-styrene block copolymer and the tackifier resin is preferably 1:2.2 to 1:3.8, and more preferably 1:2.4 to 1:3.5. If the content proportion of the tackifier resin with respect to the styrene-isoprene-styrene block copolymer is too small, the facial patch may not be applied over a long period of time onto the skin of the face that overly secretes sebum. If the content proportion of the tackifier resin is too large, when the facial patch is removed, residual adhesive may remain, or skin irritation may become severe, causing reddening of the skin.

The tackifier resin is not particularly limited as long as it is a tackifier resin that is conventionally used in rubber-based pressure-sensitive adhesives, and one kind or plural kinds thereof may be incorporated. Examples include terpene resins [for example, YS RESIN PX and CLEARON P (hydrogenated terpene resin) manufactured by Yasuhara Chemical Co., Ltd.], rosin resins [for example, KE-311, KE-100, and SUPER ESTER S-100 (rosin ester) manufactured by Arakawa Chemical Industries, Ltd., FORAL 105 (hydrogenated rosin ester) manufactured by Pinova, Inc.], coumarone-indene resins, petroleum resins, alicyclic saturated hydrocarbon resins [for example, ARKON (registered trademark) P-100 manufactured by Arakawa Chemical Industries, Ltd.], and hydrogenated alicyclic hydrocarbons (for example, ESCOREZ 5300 manufactured by Tonex Co., Ltd.). From the viewpoint of cohesive force, a terpene resin is preferred.

[Softening Agent]

The pressure-sensitive adhesive layer of the facial patch of the present invention contains a styrene-isoprene-styrene block copolymer, a tackifier resin, and a softening agent, and the content of the softening agent is 40% to 60% by mass. That is, as the pressure-sensitive adhesive layer of the facial patch of the present invention contains 40% to 60% by mass of a softening agent, the pressure-sensitive adhesive layer can enhance the followability of the facial patch to the skin, can adjust the adhesive force, and can reduce skin irritation. Therefore, a facial patch which can be applied over a long period of time onto the skin of the face that overly secretes sebum and which has less residual adhesive and is less irritating to the skin, is provided. The content of the softening agent is preferably 40% to 58% by mass, and more preferably 40% to 55% by mass. If the content proportion of the softening agent is too small, followability of the facial patch to the skin is decreased, and there is a risk that the pain at the time of removal may increase. If the content proportion of the softening agent is too large, there is a risk that residual adhesive may remain at the time of removal.

The softening agent is not particularly limited as long as it is a softening agent that is conventionally used in rubber-based pressure-sensitive adhesives, and examples thereof include softening agents such as liquid paraffin, liquid polybutene, liquid polyisobutylene, castor oil, cottonseed oil, palm oil, coconut oil, silicone oils, and process oils. From the viewpoint of exhibiting an effective softening action, a softening agent that is liquid at room temperature is preferred, and from the viewpoints of safety and compatibility with the styrene-isoprene-styrene block copolymer, liquid paraffin is particularly preferred.

[Drug and the Like]

The pressure-sensitive adhesive layer of the facial patch of the present invention contains a styrene-isoprene-styrene block copolymer, a tackifier resin and a softening agent at predetermined amounts and proportions, and may also contain various additives, if necessary, while the pressure-sensitive adhesive layer can contain even a drug. The drug is not particularly limited as long as it is a drug that is used by being incorporated into the pressure-sensitive adhesive layer of a facial patch. However, the drugs included in ointments, creams, sprays and the like that are used for the face, nasal mucosa and the like, as well as the active ingredients included in cosmetics and quasi-drugs that are effective for freckles, wrinkles and the like, are preferred. Examples thereof include anti-inflammatory agents (pyridoxine dicaprylate, dipotassium glycyrrhizinate, pyridoxine dipalmitate, glycyrrhizic acid, diphenhydramine hydrochloride, a cork tree bark extract, glycyrrhetinyl stearate, lysozyme chloride, aminocaproic acid, a reishi mushroom extract, a coix seed extract, a melilot extract, a peony extract, a dong quai extract, a dong quai root extract, a enidium rhizome extract, a geranium, herb extract, allantoin, an arnica extract, and the like), antibacterial agents (shikonin, hinokitiol, cedrol, benzalkonium chloride, benzethonium chloride, photosensitizing dye No. 201, adipic acid, and the like), sebum secretion inhibitors (estradiol, vitamin B2, vitamin B6, a royal jelly extract, riboflavin, and the like), oil absorbent porous powders (porous nylon powders, porous cellulose powders, and the like), sebum absorbents (kaolin, talc, clay, zinc oxide, and the like), keratin remover (salicylic acid, sulfur, bentonite, cyclodextrin, and the like), antioxidants (dibutylhydroxytoluene, tocopherol acetate, ascorbic acid, benzoic acid, parabens, benzalkonium chloride, benzethonium chloride, and the like), skin roughness improving agents (an *Arnica montana* extract, a licorice extract, retinol, dipotassium glycyrrhizinate, a peony extract, a sage leaf extract, a loquat leaf extract, a rosemary extract, and the like), oxidation inhibitors (vitamins, butylhydroxytoluene, and the like), various analgesic antiphlogistic agents, antihistamines, corticosteroid agents, humectants, vitamins, fragrances, and cosmetic components.

[Other Additives]

Furthermore, the pressure-sensitive adhesive layer of the facial patch of the present invention may contain other additives as necessary. The other additives are not particularly limited as long as they are additives conventionally used by being incorporated into the pressure-sensitive adhesive layer of a facial patch. Examples thereof include a transdermal absorption enhancer, a filler, an ultraviolet absorber, a solubilizer, a colorant, and a plasticizer.

[Thickness of Pressure-sensitive Adhesive Layer]

The thickness of the pressure-sensitive adhesive layer included in the facial patch of the present invention is in the range of 1 μm to 50 μm, and is preferably a thickness in the range of 3 μm to 45 μm, and more preferably 5 μm to 40 μm. As the pressure-sensitive adhesive layer included in the facial patch of the present invention satisfies the following conditions (a-1) to (a-3):

(a-1) the pressure-sensitive adhesive layer contains a styrene-isoprene-styrene block copolymer, a tackifier resin, an a softening agent;

(a-2) the ratio (mass ratio) of the styrene-isoprene-styrene block copolymer and the tackifier resin is 1:2 to 1:4; and (a-3) the content of the softening agent is 40% to 60% by mass, a facial patch which has suitable adhesiveness, can be applied over a long period of time onto the skin of the face that secretes a large amount of sebum, has less residual adhesive, and is less irritating to the skin, can be provided. The pressure-sensitive adhesive layer included in the facial patch of the present invention further satisfies the following conditions (a-2') and (a-3'):

(a-2') the ratio (mass ratio) of the styrene-isoprene-styrene block copolymer and the tackifier resin is 1:2.4 to 1:3.5; and (a-3') the content of the softening agent is 40% to 55% by mass, and a superior effect is provided.

[Thicknesses of Support and Pressure-sensitive Adhesive Layer]

The facial patch of the present invention is such that the total thickness of the support and the pressure-sensitive adhesive layer is in the range of 2 μm to 120 μm, and is preferably a thickness in the range of 6 μm to 100 μm, and more preferably 10 μm to 80 μm. If the total thickness of the support and the pressure-sensitive adhesive layer is too small, the strength of the facial patch is insufficient, and when the facial patch is applied onto the skin of the face, or when the facial patch is removed from the skin of the face, the facial patch may be torn off. Furthermore, the facial patch may have insufficient tackiness to the skin of the face, and may have insufficient adhesiveness to the face that overly secretes sebum. On the other hand, if the total thickness of the support and the pressure-sensitive adhesive layer is too large, it is difficult for the facial patch to adhere along the minute irregularities of the skin surface of the face, such as skin furrows, the state of adhesion becomes conspicuous, and the sense of discomfort is likely to increase. In addition, when the facial patch is removed from the skin of the face, the skin may be damaged, or the removal may cause pain.

3. Release Layer

The facial patch of the present invention is a facial patch which includes a support, a pressure-sensitive adhesive layer, and a release layer in this order. That is, the facial patch of the present invention includes a release layer adjacent to the pressure-sensitive adhesive layer, in order to protect the pressure-sensitive adhesive layer until the facial patch, specifically the pressure-sensitive adhesive layer, is applied onto the skin.

The release layer according to the present invention is not particularly limited, and any release layer that is generally used under the names of release paper, release film, peelable paper, peelable film, release liner, or the like in the technical field of facial patches, more specifically adhesive patches (pressure-sensitive adhesive tapes), can be used. Specific examples include a polyethylene terephthalate film having a silicone-treated surface, and a laminate of paper and a polyethylene sheet having a silicone-treated surface. The release layer may be produced into a sheet of two or more sheets having the same thickness or different thicknesses, so as to be used to protect the pressure-sensitive adhesive layer. Furthermore, in order to enhance handleability (that is, reusability from the pressure-sensitive adhesive layer), the release layer may also be provided with a cut line, or may be formed to have a larger area than the facial patch, with gripping parts being provided at the peripheral edge. Furthermore, for the purpose of enhancing handleability or enhancing print suitability, the release layer may be provided with surface irregularities by a sandblasting treatment or the like, on the surface of the release layer, which faces the pressure-sensitive adhesive layer, or on the surface on the opposite side of the pressure-sensitive adhesive layer. Furthermore, the release layer may be provided as one large sheet, and a plural number of a combination of a pressure-sensitive adhesive layer, a support and a carrier film may be arranged on the sheet. In this case, the release layer is shared by plural adhesive patches.

Furthermore, the release layer can also be used in order to facilitate the formation of the pressure-sensitive adhesive layer in the method for producing a facial patch of the present invention, as will be described below. That is, a laminated sheet including a pressure-sensitive adhesive layer, and a release layer is produced by a method of applying a pressure-sensitive adhesive composition for forming a pressure-sensitive adhesive layer, which contains a styrene-isoprene-styrene block copolymer, a tackifier resin and a softening agent, on the surface of a release layer prepared in advance, or the like. Subsequently, a support is laminated on the surface of the pressure-sensitive adhesive layer, and thereby a facial patch including a support, a pressure-sensitive adhesive layer, and a release layer in this order can be obtained.

The thickness of the release layer can be appropriately set and is not particularly limited; however, the thickness is usually 20 μm or more, and preferably 40 μm or more, and the upper limit is about 500 μm.

4. Carrier Film

The facial patch of the present invention is a facial patch including a support, a pressure-sensitive adhesive layer, and a release layer in this order, and by providing a carrier film adjacent to the support to be on the surface of the support that is on the opposite side of the pressure-sensitive adhesive layer, handleability of the facial patch and attachability to the skin can be enhanced. That is, when the facial patch is applied onto the skin, there may be occasions in which the support has wrinkles formed therein, or the facial patch is folded so that a part of the pressure-sensitive adhesive layer is adhered to another part of the same layer. However, when the facial patch includes a carrier film adjacent to the support, and thereby the facial patch is produced to include a carrier film, a support, a pressure-sensitive adhesive layer, and a release layer in this order, shape retention of the facial patch is improved, and therefore, such a problem can be prevented. The carrier film is used such that the release layer is first peeled off from the aforementioned facial patch, the pressure-sensitive adhesive layer is pressed against the skin of the face to apply the facial patch, and then the carrier film is peeled off from the support.

The material for forming the carrier film is not particularly limited, and the same material as the material that forms the release layer can be used. For example, the carrier film can be formed using films formed from various thermoplastic resins, and for example, films formed from polyurethane, polyethylene, polypropylene, an ionomer, polyamide, polyvinyl chloride, polyvinylidene chloride, an ethylene-vinyl acetate copolymer, a thermoplastic polyester, and polytetrafluoroethylene can be used. Furthermore, laminates of these films and paper can be used. The carrier film is preferably a polyester film from the viewpoint of enhancing handleability and attachability to the skin, and in order to make it easier to peel off the carrier film from the support after the facial patch is applied, it is preferable that the surface on the support side is provided with matt finish. The carrier film and the support are formed so as to be detachable by thermal compression, pressure-sensitive adhesion or the like. In order to adjust the peeling force between the carrier film and the support, a pressure-sensitive adhesive, a liquid plasticizer, a mold releasing agent or the like may be applied on the surface of the carrier film on the side facing the support, or the surface may be subjected to any other surface treatment.

The thickness of the carrier film can be suitably set and is not particularly limited; however, the thickness is usually 20 μm or more, and preferably 40 μm or more, and the upper limit is about 500 μm.

[Size of Carrier Film]

In a case in which the facial patch of the present invention includes a carrier film, the size of the carrier film may be the same as that of the support, or may also be larger than the size of the support. When the carrier film is larger than the support, it is easier to peel off the pressure-sensitive adhesive layer of the facial patch from the release layer by utilizing the carrier film as a grip section of the patch, and the pressure-sensitive adhesive layer of the facial patch can be applied onto the skin, without having fingers stuck to the pressure-sensitive adhesive. Here, the phrase "the carrier film is larger than the support" means a state in which the whole surface of the carrier film does not cover the support; in other words, the phrase means that the carrier film has some area that does not cover the support. For example, the carrier film cab be included so as to adopt embodiments such as a case in which the area of the carrier film is larger than the area of the support (in this case, a portion of the carrier film covers the support), as well as a case in which the carrier film is formed in a patterned form such as a lattice pattern, and an edge of the lattice protrudes from the support, and a case in which the carrier film covers the support such that the marginal part of the support protrudes from the support. The carrier film may be provided so as to cover such that the support is divided into plural sheets or is in a state of being partially overlapping. Furthermore, a sheet provided with a lead or a cut line for enhancing handleability may also be disposed on a surface of the carrier film (surface on the opposite side of the support).

[Peeling Force of Release Layer and Peeling Force of Carrier Film]

The force required to peel off the release layer from the pressure-sensitive adhesive layer of the facial patch (peeling force of the release layer) is set to be smaller than the force for peeling off the carrier film from the support of the facial patch (peeling force of the carrier film). When the peeling force is set as such, since the carrier film remains integrally on the support after the release layer is peeled off from the pressure-sensitive adhesive layer of the facial patch, the facial patch has rigidity to a certain extent until the facial patch is applied onto the skin, and therefore, satisfactory handleability is obtained.

5. Facial Patch

The facial patch of the present invention is a facial patch including a support, a pressure-sensitive adhesive layer, and a release layer in this order, wherein (a) the pressure-sensitive adhesive layer satisfies the following conditions (a-1) to (a-3):

(a-1) the pressure-sensitive adhesive layer contains a styrene-isoprene-styrene block copolymer, a tackifier resin, and a softening agent;

(a-2) the ratio (mass ratio) of the styrene-isoprene-styrene block copolymer and the tackifier resin is 1:2 to 1:4; and (a-3) the content of the softening agent is 40% to 60% by mass; and (b) the support has elastic moduli with a Young's modulus of 0.01 GPa to 0.5 GPa. The facial patch of the present invention can give an effect that a facial patch which can be applied over a long period of time onto the skin of the face that secretes a large amount of sebum and which has less residual adhesive and is less irritating to the skin, can be provided by a characteristic combination of a pressure-sensitive adhesive layer and a support having the configuration described above. Particularly, the facial patch of the present invention gives a superior effect that the styrene-isoprene-styrene block copolymer described above includes a high-styrene content styrene-isoprene-styrene block copolymer.

Specifically, the facial patch of the present invention has favorable adhesiveness and flexibility, has less pain at the time of removal, and has less residual adhesive after removal. Furthermore, more specifically, the effects of the facial patch of the present invention can be confirmed by the adhesive force measured by a predetermined method, the probe tack, and the area of the corneous tissues removed.

[Attachability]

The facial patch of the present invention has excellent attachability that is evaluated by the following method. That is, test specimens cut out to a size of 15 mm in width×50 mm in length (rectangle having an area of 7.5 cm$^2$) from facial patches of the present invention are applied onto seven male and female adult testees on the cheeks that have been wiped off to remove water after face washing, and the test specimens are left to stand for 12 hours (hereinafter, may be referred to as "after application for 12 hours"). The testees are asked to evaluate the facial patch, and thus an evaluation on the attachability of the facial patch is carried out on the basis of the following criteria. When a facial patch is rated as AA or A, it can be said that the facial patch has excellent attachability.

<Evaluation Criteria for Attachability>

AA: Six to seven subjects evaluated the attachability to be strong.

A: four to five subjects evaluated the attachability to be strong.

B: Two to three subjects evaluated the attachability to be strong.

C: One or zero subjects evaluated the attachability to be strong.

[Flexibility]

The facial patch of the present invention has excellent flexibility that is evaluated according to the following method. That is, the seven testees to whom the test specimens of the facial patch have been applied are asked to evaluate flexibility after application for 12 hours, and thus an evaluation on the flexibility of the facial patch is carried out on the basis of the following criteria. When a facial patch is rated as AA or A, it can be said that the facial patch has excellent flexibility.

<Evaluation Criteria for Flexibility>

AA: Six to seven subjects evaluated that the facial patch was flexible.

A: Four to five subjects evaluated that the facial patch was flexible.

B: Two to three subjects evaluated that the facial patch was flexible.

C: One or zero subjects evaluated that the facial patch was flexible.

[Pain Upon Removal]

The facial patch of the present invention is excellent in view of causing less pain at the time of removal, which is evaluated by the following method. That is, the seven testees to whom the test specimens of the facial patches have been applied are asked to evaluate whether there is pain when the facial patch is removed after application for 12 hours, and the pain is evaluated based on the following four-point scale: 0 (no pain is felt), 1 (slight pain is felt), 2 (pain is felt more strongly than grade 1), and 3 (pain is felt strongly). The average value of the seven subjects is rounded off, and thus an evaluation on the pain at the time of removal of the patch is carried out on the basis of the following criteria. When a facial patch is rated as AA or A, it can be said that the facial patch is excellent with less pain at the time of removal.

<Evaluation Criteria for Pain Upon Removal>

AA: The average value of the four-point scale is 0.

A: The average value of the four-point scale is 1.

B: The average value of the four-point scale is 2.

C: The average value of the four-point scale is 3.

[Residual Adhesive After Removal]

The state of the residual adhesive on the cheeks onto which the facial patches have been applied (hereinafter, may be simply referred to as "residual adhesive") of the seven subjects to whom the above-described test specimens of the facial patches have been applied thereto, after the facial patches are applied for 12 hours and then removed, is visually inspected. The residual adhesive is evaluated by a four-point scale: 0 (no residual adhesive), 1 (slight residual adhesive recognized), 2 (more residual adhesive recognized, compared with 1), and 3 (residual adhesive recognized to a large extent), and the average values of the seven subjects are rounded off. Thus, an evaluation of the residual adhesive of the facial patches is carried out on the basis of the following criteria. When, a facial patch is rated as AA or A, it can be said that the facial patch has excellent feeling of use.

<Evaluation Criteria of Residual Adhesive>
AA: The average value of the four-point scale is 0.
A: The average value of the four-point scale is 1.
B: The average value of the four-point scale is 2.
C: The average value of the four-point scale is 3.

[Adhesive Force]

The facial patch of the present invention has an adhesive force in the range of 0.5 to 3 N/15 mm, preferably in the range of 0.5 to 2.7 N/15 mm, and more preferably in the range of 0.6 to 2.5 N/1.5 mm, in a 180-degree peel test against a BA-SUS plate (bright annealed stainless steel) according to JIS Z0237. As the facial patch of the present invention has an adhesive force against a BA-SUS plate in the range described above, when the facial patch is applied onto the skin of the face, the facial patch is not easily peeled off by an external force such as the movement of the skin, and no resistance or pain is felt when the facial patch is removed from the skin surface of the face. If the adhesive force against a BA-SUS plate is too large, there is a risk that resistance or pain may be felt when the facial patch is removed from the skin surface of the face. The 180-degree peel test against a BA-SUS plate is to measure the adhesive force obtainable when a test specimen of a facial patch cut to a size of 15 mm in width is attached to a BA-SUS plate, a rubber roll weighing 2 kg is moved back and forth thereon two times at a speed of 300 mm/min, and the test specimen is stripped off within one minute under the conditions of a peeling rate of 300 mm/min in the 180-degree direction, with an Instron type tensile tester (average value of n=3).

[Probe Tack]

The facial patch of the present invention has a probe tack of the pressure-sensitive adhesive layer preferably in the range of 1.5 to 5 N/5 mmϕ, and more preferably in the range of 1.6 to 4 N/5 mmϕ. As the pressure-sensitive adhesive layer of the facial patch of the present invention has a probe tack in the range described above, when the facial patch is applied onto the skin of the face, the facial patch is not easily peeled off even by an external force such as the movement of the skin, and there is no risk that resistance or pain is felt when the facial patch is removed from the skin. The probe tack described above is determined by measuring the force required to detach a cylindrical probe having a diameter of 5 mm in a direction perpendicular to the surface of adhesion according to the probe tack testing method described in JIS Z0237 (1996 edition), using a probe tack tester manufactured by Nichiban Co., Ltd. (average value of n=3).

[Area of Corneous Tissue Removal]

The facial patch of the present invention can be applied over a long period of time onto the skin of the face, has less residual adhesive, and is less irritating to the skin. The facial patch also has an area of the corneous tissue removal at the time of removing the facial patch from the skin of the face applied with the facial patch, of 45% or less, preferably 40% or less, and more preferably 35% or less. The area of the corneous tissue removal of a facial patch is measured by the following method. That is, test specimens cut out to a size of 15 mm in width×50 mm in length from the facial patch of the present invention, are applied onto seven male and female adult testees on the cheeks that have been wiped off to remove water after face washing, and after the test specimens are left to stand for 12 hours, the test specimens are removed. The sum of the areas of corneous tissues adhering to (the pressure-sensitive adhesive layer of) the facial patch after removal is measured, and the ratio of the area of the corneous tissue removal with respect to the area of the patch is calculated (unit: %).

[Shape, Size and Thickness of Patch]

The facial patch of the present invention is a facial patch including a support, a pressure-sensitive adhesive layer, and a release layer in this order, and there are no particular limitations on the shape as long as the facial patch has the general characteristics described above. Thus, the facial patch may be a facial patch having a predetermined shape, a facial patch in a roll form, or a facial patch enclosed in an envelope. Specific examples of the predetermined shape include a rectangular shape, an elliptical shape, a crescent shape, a circular shape, a horseshoe shape, and an annular shape. For a facial patch having a predetermined shape with corners on the periphery, the corners on the periphery may be provided with appropriate R. There are no particular limitations on the size of the patch, and the patch may have a size to be applied onto the entire surface or the entire cheek, or may have a small size to be applied onto acne areas. For example, the area of application per sheet can be usually adjusted to the range of 0.5 $cm^2$ to 100 $cm^2$, preferably to the range of 1 $cm^2$ to 50 $cm^2$, and more preferably to the range of 1 $cm^2$ to 30 $cm^2$. The thickness of the facial patch of the present invention, (total thickness of the support, pressure-sensitive adhesive layer and release layer) is usually 22 μm to 400 μm, and in many cases, the thickness is in the range of 40 μm to 300 μm.

6. Method for Producing Facial Patch

The facial patch of the present invention is a facial patch including a support, a pressure-sensitive adhesive layer, and a release layer in this order, and as long as the aforementioned facial patch characterized in that:

(a) the pressure-sensitive adhesive layer satisfies the following conditions (a-1) to (a-3):

(a-1) the pressure-sensitive adhesive layer contains a styrene-isoprene-styrene block copolymer, a tackifier resin, and a softening agent;

(a-2) the ratio (mass ratio) of the styrene-isoprene-styrene block copolymer and the tackifier resin is 1:2 to 1:4; and (a-3) the content of the softening agent is 40% to 60% by mass; and (b) the support has elastic moduli with a Young's modulus of 0.01 GPa to 0.5 GPa, can be obtained, the method for production thereof is not limited. From the viewpoint of the production efficiency, a method for producing a facial patch including a step of forming a pressure-sensitive adhesive layer on the upper surface of a release layer is preferred. Specifically, it is preferable to follow a method of coating the upper surface of a release layer that has been formed in advance, with a pressure-sensitive adhesive for forming a pressure-sensitive adhesive layer, that is, a pressure-sensitive adhesive containing a styrene-isoprene-styrene block copolymer, a tackifier resin, and a softening agent, while causing the release layer to run in one direction, forming a pressure-sensitive adhesive layer by drying and removal, and then laminating thereon a support (may have a carrier film laminated thereon) having elastic moduli with a Young's modulus of 0.01 GPa to 0.5 GPa.

Regarding the facial patch of the present invention, for example, a facial patch in a roll form may be obtained by producing a facial patch including a carrier film, a support, a pressure-sensitive adhesive layer and a release layer in this order laminated together by the method described above or the like, and then winding the facial patch into a roll form; or a facial patch having an approximately rectangular shape or a circular shape may be obtained by cutting the facial patch into a desired shape, for example, an approximately rectangular shape or a circular shape. Furthermore, the facial patch may also be obtained in a state of being enclosed in an envelope.

7. Use of Facial Patch

The facial patch of the present invention is a facial patch which adheres along the irregularities of the skin surface of the face, and for which the applied portion is not conspicuous, and application onto the face that overly secretes sebum is maintained over a long period of time. Therefore, the facial patch of the present invention can be used as a facial patch for T-Zone or U-zone which is applicable to the so-called T-zone or U-zone, that is, (i) the T-shaped area extending from the forehead to the ridge of the nose, where sebum is easily accumulated because secretion of sebum occurs more than other portions, makeup running or greasiness is conspicuous, or acne can easily develop; or (ii) the U-shaped area such as the chin, where secretion of sebum occurs less, but acne can easily develop in adult men and women. Furthermore, the facial patch can also be used as a facial patch for acne treatment, which is applied onto a portion of acne developed as a result of inflammation cause by the interaction between skin pores (hair follicles) causing inflammation, and sebum, hormones and bacteria. Particularly, in the case of obtaining a facial patch for acne treatment, a facial patch which is not peeled off for at least 12 hours, even if sebum is secreted from the skin of acne portions and the vicinity thereof, can be provided.

Furthermore, when the facial patch of the present invention is applied onto the face after sebum is removed by washing the face, sebum accumulation at the applied portion or greasiness can be prevented. Also, when the patch is applied after face washing, and makeup is put on the patch, the facial patch can cover the skin underneath the facial patch and make the skin inconspicuous. Therefore, the facial patch can be used as a facial patch for application after face washing. Even if no active ingredient is incorporated into the pressure-sensitive adhesive, the facial patch of the present invention can be used for wrinkle care, lifting of the skin, freckle covering and the like. Furthermore, it is more effective if the pressure-sensitive adhesive that forms the pressure-sensitive adhesive layer is a pressure-sensitive adhesive containing drugs such as described above. Furthermore, the facial patch of the present invention can be used for cosmetic purposes when the pressure-sensitive adhesive that forms the pressure-sensitive adhesive layer contains components that are used in cosmetic applications, for example, allantoin, lecithin, amino acids, kojic acid, proteins, saccharides, hormones, placenta extracts; and cosmetic components such as extract components of aloe vera, sponge cucumber, licorice and the like, various vitamins, diphenhydramine hydrochloride, diphenhydramine salicylate, diphenhydramine tannate, triprolidine hydrochloride, mequitazine, chlorophenylamine maleate, clemastine fumarate, promethazine hydrochloride, tranilast, sodium cromoglycate, ketotifen, arylsulfatase B, bufexamac, butyl flufenamate, ibuprofen, indomethacin, aspirin, flurbiprofen, ketoprofen, piroxicam, and ibuprofen piconol. Furthermore, a sunscreen agent, a foundation and the like can be applied over the facial patch.

EXAMPLES

Hereinafter, the present invention will be described specifically by way of Examples and Comparative Examples; however, the present invention is not intended to be limited to these Examples. The characteristics of the facial patch of the present invention and the various layers included in the patch, and the methods for measuring physical properties are as follows.

[Thickness]

The thicknesses of the facial patch, and the carrier film, support, pressure-sensitive adhesive layer and release layer included in the patch were measured using a dial type thickness gauge.

[Young's Modulus]

The Young's modulus of the support was measured according to ASTM-D-882.

[Percentage Content of Styrene and Amount of Diblocks]

The percentage content of styrene in the styrene-isoprene-styrene block copolymer
was measured by infrared spectroscopy, and the amount of diblocks was measured by a GPC
method.

[Attachability]

Attachability of a facial patch was evaluated by the following method. That is, test specimens cut out to a size of 15 mm in width×50 mm in length (rectangle having an area of 7.5 $cm^2$) from a facial patch were applied onto seven male and female adult testees on the cheeks that had been wiped off to remove water after face washing, and the test specimens were left to stand for 12 hours. The testees were asked to evaluate the facial patch after standing for 12 hours (after application for 12 hours), and thus an evaluation on the attachability of the facial patch was carried out on the basis of the following criteria.

<Evaluation Criteria for Attachability>

AA: Six to seven subjects evaluated the attachability to be strong.

A: Pour to five subjects evaluated the attachability to be strong.

B: Two to three subjects evaluated the attachability to be strong.

C: One or zero subjects evaluated the attachability to be strong.

[Flexibility]

Flexibility of a facial patch was evaluated by the following method. That is, the seven testees to whom the test specimens of the facial patch had been applied were asked to evaluate flexibility were asked to evaluate flexibility after application for 12 hours, and thus an evaluation on the flexibility of the facial patch was carried out on the basis of the following criteria.

<Evaluation Criteria for Flexibility>

AA: Six to seven subjects evaluated that the facial patch was flexible.

A: Four to five subjects evaluated that the facial patch was flexible.

B: Two to three subjects evaluated that the facial patch was flexible.

C: One or zero subjects evaluated that the facial patch was flexible.

[Pain Upon Removal]

The pain at the time of removal of the facial patch was evaluated by the following method. That is, the seven subjects to whom the test specimens of the facial patches had been applied were asked to evaluate whether there was pain when the facial patch was removed after application for 12 hours, and the pain was evaluated based on the following four-point scale: 0 (no pain is felt), 1 (slight pain is felt), 2 (pain is felt more strongly than grade 1), and 3 (pain is felt strongly). The average value of the seven subjects was rounded off, and thus an evaluation on the pain at the time of removal of the patch was carried out on the basis of the following criteria.

<Evaluation Criteria for Pain Upon Removal>
AA: The average value of the four-point scale is 0.
A: The average value of the four-point scale is 1.
B: The average value of the four-point scale is 2.
C: The average value of the four-point scale is 3.

[Residual Adhesive After Removal]

Residual adhesive after removal of the facial patch was evaluated by the following method. That is, the state of the residual adhesive on the cheeks onto which the facial patches had been applied of the seven subjects to whom the test specimens of the facial patches had been applied thereto, after the facial patches were applied for 12 hours and then removed, was visually inspected. The residual adhesive was evaluated by a four-point scale: 0 (no residual adhesive), 1 (slight residual adhesive recognized), 2 (more residual adhesive recognized, compared with 1), and 3 (residual adhesive recognized to a large extent), and the average values of the seven subjects were rounded off. Thus, an evaluation of the residual adhesive of the facial patches was carried out on the basis of the following criteria.

<Evaluation Criteria for Residual Adhesive>
AA: The average value of the four-point scale is 0.
A: The average value of the four-point scale is 1.
B: The average value of the four-point scale is 2.
C: The average value of the four-point scale is 3.

[Adhesive Force (Adhesive Force Against BA-SUS Plate)]

The adhesive force of the facial patch (adhesive patch against BA-SUS plate) was measured by performing a 180-degree peel test, was carried out according to JIS Z0237. That is, a test specimen of a facial patch cut to a size of 15 mm in width×70 mm in length was attached to a BA-SUS plate, a rubber roll weighing 2 kg is moved back and forth thereon two times at a speed of 300 mm/min, and the test specimen is stripped off within one minute under the conditions of a peeling rate of 300 mm/min in the 180-degree direction, with an Instron type tensile tester (unit: N/15 mm) (average value of n=3).

[Probe Tack of Pressure-sensitive Adhesive Layer of Facial Patch]

The probe tack of the pressure-sensitive adhesive layer of a facial patch was determined by measuring the force required to detach a cylindrical probe having a diameter of 5 mm in a direction perpendicular to the surface of adhesion according to the probe tack testing method described in JIS Z0237 (1996 edition) as reference, using a probe tack tester manufactured by Nichiban Co., Ltd. (average value of n=3).

[Area of Corneous Tissue Removal]

Regarding the area of corneous tissue removal of a facial patch, test specimens cut out to a size of 15 mm in width×50 mm in length from the facial patch of the present invention, were applied onto seven male and female adult testees on the cheeks that had been wiped off to remove water after face washing, and after the test specimens were left to stand for 12 hours, the test specimens were removed. The sum of the areas of corneous tissues adhering to (the pressure-sensitive adhesive layer of) the facial patch after removal was measured, and the ratio of the area of the corneous tissue removal with respect to the area of the patch was calculated (unit: %).

Example 1

100 parts by mass of a styrene-isoprene-styrene block copolymer (JSR SIS5002 manufactured by JSR Corp., percentage content of styrene: 22% by mass, amount of diblocks: 15% by mass), 250 parts by mass of a terpene resin (YS RESIN manufactured by Yasuhara Chemical Co., Ltd.) as a tackifier resin, and 350 parts by mass of liquid paraffin (HICALL (registered trademark) M-352 manufactured by Kaneda Co., Ltd.) as a softening agent were mixed, and the mixture was dissolved in a solution of toluene/acetone=8/2. Thus, a coating liquid for forming a pressure-sensitive adhesive layer having a solid content of 57% by mass was prepared. This coating liquid was applied on one surface of a peelable paper (silicone-treated polyethylene terephalate film, thickness 75 µm) intended for forming a release layer, using a bar coater so as to obtain a thickness after drying of 20 µm, and then the coating liquid was dried. Thus, a laminate composed of a release layer and a pressure-sensitive adhesive layer was obtained. Subsequently, a low-density polyethylene film (Young's modulus 0.12 GPa) having a thickness of 35 µm as a support was disposed on the upper surface of the pressure-sensitive adhesive layer, superimposed with the pressure-sensitive adhesive layer, and the laminate was cut. Thus, a facial patch having a thickness of 130 µm and including a support, a pressure-sensitive adhesive layer, and a release layer in this order was produced. For this facial patch, attachability, flexibility, pain at the time of removal, residual, adhesive after removal, adhesive force against a BA-SUS plate, probe tack, and area of corneous tissue removal (hereinafter, may be collectively referred to as "general characteristics") were analyzed, and the results of evaluation are presented in Table 1 together with the composition of the pressure-sensitive adhesive layer.

Example 2

A facial patch was produced in the same manner as in Example 1, except that 300 parts by mass of liquid paraffin as a softening agent was incorporated. For this facial patch, the general characteristics were analyzed, and the results of evaluation are presented in Table 1 together with the composition of the pressure-sensitive adhesive layer.

Example 3

A facial patch was produced in the same manner as in Example 1, except that 250 parts by mass of liquid paraffin as a softening agent was incorporated. For this facial patch, the general characteristics were analyzed, and the results of evaluation are presented in Table 1 together with the composition of the pressure-sensitive adhesive layer.

Example 4

A facial patch was produced in the same manner as in Example 2, except that the support was changed to a low-density polyethylene film (Young's modulus 0.13 GPa) having a thickness of 15 µm. For this facial patch, the general characteristics were analyzed, and the results of evaluation are presented in Table 1 together with the composition of the pressure-sensitive adhesive layer.

Example 5

A facial patch was produced in the same manner as in Example 2, except that 100 parts by mass of a styrene-isoprene-styrene block copolymer (JSR SIS5000 manufactured by JSR Corp., percentage content of styrene: 14% by mass, amount of diblocks: 26% by mass) was incorporated. For this facial patch, the general characteristics were analyzed, and the results of evaluation are presented in Table 1 together with the composition of the pressure-sensitive adhesive layer.

Example 6

A facial patch was produced in the same manner as in Example 1, except that 200 parts by mass of a terpene resin as a tackifier resin was incorporated. For this facial patch, the general characteristics were analyzed, and the results of evaluation are presented in Table 1 together with the composition of the pressure-sensitive adhesive layer.

Example 7

A facial patch was produced in the same manner as in Example 3, except that the terpene resin as a tackifier resin was changed to a rosin resin (KE-311 manufactured by Arakawa Chemical Industries, Ltd.). For this facial patch, the general characteristics were analyzed, and the results of evaluation are presented in Table 1 together with the composition of the pressure-sensitive adhesive layer.

Comparative Example 1

A facial patch was produced in the same manner as in Example 1, except that 150 parts by mass of liquid paraffin as a softening agent was incorporated. For this facial patch, the general characteristics were analyzed, and the results of evaluation are presented in Table 1 together with the composition of the pressure-sensitive adhesive layer.

Comparative Example 2

A facial patch was produced in the same manner as in Example 1, except that 817 parts by mass of liquid paraffin as a softening agent was incorporated. For this facial patch, the general characteristics were analyzed, and the results of evaluation are presented its Table 1 together with the composition of the pressure-sensitive adhesive layer.

Comparative Example 3

A facial patch was produced in the same manner as in Example 3, except that 150 parts by mass of a terpene resin as a tackifier resin was incorporated. For this facial patch, the general characteristics were analyzed, and the results of evaluation are presented in Table 1 together with the composition of the pressure-sensitive adhesive layer.

Comparative Example 4

A facial patch was produced in the same manner as in Example 2, except that the support was changed to a polyethylene terephthalate film [LUMIRROR (registered trademark) S-10 manufactured by Toray Industries, Inc., Young's modulus: 4.7 GPa] having a thickness of 25 μm. For this facial patch, the general characteristics were analyzed, and the results of evaluation are presented in Table 1 together with the composition of the pressure-sensitive adhesive layer.

TABLE 1

| Example/ Comparative Example | Support | Composition of pressure-sensitive adhesive layer (parts by mass) SIS/tackifier resin/softening agent (mass ratio) | Compounding ratio (mass %) SIS | Tackifier resin | Softening agent | Attachability |
|---|---|---|---|---|---|---|
| Example 1 | Polyethylene (thickness 35 μm) | 100/250/350 | 14.3 | 35.7 | 50.0 | AA |
| Example 2 | Polyethylene (thickness 35 μm) | 100/250/300 | 15.4 | 38.5 | 46.2 | AA |
| Example 3 | Polyethylene (thickness 35 μm) | 100/250/250 | 16.7 | 41.7 | 41.7 | AA |
| Example 4 | Polyethylene (thickness 15 μm) | 100/250/300 | 15.4 | 38.5 | 46.2 | AA |
| Example 5 | Polyethylene (thickness 35 μm) | 100/250/300 (SIS: percentage content of styrene 14 mass %) | 15.4 | 38.5 | 46.2 | AA |
| Example 6 | Polyethylene (thickness 35 μm) | 100/250/350 | 15.4 | 30.8 | 53.8 | AA |
| Example 7 | Polyethylene (thickness 35 μm) | 100/250/250 (tackifier resin is rosin resin) | 16.7 | 41.7 | 41.7 | AA |
| Comparative Example 1 | Polyethylene (thickness 35 μm) | 100/250/150 | 20.0 | 50.0 | 30.0 | AA |
| Comparative Example 2 | Polyethylene (thickness 35 μm) | 100/250/817 | 8.6 | 21.4 | 70.0 | B |
| Comparative Example 3 | Polyethylene (thickness 35 μm) | 100/150/250 | 20.0 | 30.0 | 50.0 | B |
| Comparative Example 4 | Polyethylene terephthalate (thickness 25 μm) | 100/250/300 | 15.4 | 38.5 | 46.2 | B |

| Example/ Comparative Example | Flexibility | Pain upon removal | Residual adhesive after removal | Adhesive force against BA-SUS plate (N/15 mm) | Probe tack (N/5 mmφ) | Area of corneous tissue removal (%) |
|---|---|---|---|---|---|---|
| Example 1 | AA | AA | AA | 0.7 | 2.0 | 12 |
| Example 2 | AA | A | AA | 2.0 | 2.5 | 21 |
| Example 3 | AA | AA | AA | 2.4 | 2.8 | — |
| Example 4 | AA | AA | AA | 2.0 | 2.5 | 8 |
| Example 5 | AA | AA | A | 2.5 | 3.8 | 23 |

TABLE 1-continued

|  |  |  |  |  |  |  |
|---|---|---|---|---|---|---|
| Example 6 | AA | A | AA | 0.6 | 1.8 | 23 |
| Example 7 | AA | A | A | 3.2 | 4.5 | 16 |
| Comparative Example 1 | AA | B | AA | 5.6 | 4.4 | 64 |
| Comparative Example 2 | AA | AA | B | — | — | — |
| Comparative Example 3 | AA | AA | AA | 0.4 | 1.9 | — |
| Comparative Example 4 | B | AA | AA | — | — | 4 |

From Table 1, it was found that the facial patches of Examples 1 to 7, each of which is a facial patch including a support, a pressure-sensitive adhesive layer, and a release layer in this order, and in which (a) the pressure-sensitive adhesive layer satisfies the following conditions (a-1) to (a-3):

(a-1) the pressure-sensitive adhesive layer contains a styrene-isoprene-styrene block copolymer, a tackifier resin, and a softening agent;

(a-2) the ratio (mass ratio) of the styrene-isoprene-styrene block copolymer and the tackifier resin is 1:2 to 1:4; and (a-3) the content of the softening agent is 40% to 60% by mass; and (b) the support has elastic moduli with a Young's modulus of 0.01 GPa to 0.5 GPa, had excellent attachability to the skin of the face and excellent flexibility, caused no pain at the time of removal, and had no residual adhesive after removal. Furthermore, the facial patches had an adhesive force against a BA-SUS plate of 0.6 to 2.5 N/15 mm, a probe tack of 1.8 to 4.5 N/5 mmϕ, appropriate pressure-sensitive adhesiveness, and excellent characteristics with low detachability as exhibited by an area of corneous tissue removal of 8% to 23%. Therefore, it was found that a facial patch which can be applied over a long period of time onto the skin of the face that overly secretes sebum, and which has less residual adhesive and is less irritating to the skin, is provided.

Particularly, it was found that the facial patches of Examples 1 to 3 in which the pressure-sensitive adhesive layer contained a styrene-isoprene-styrene block copolymer having a percentage content of styrene of 22% by mass and an amount of diblocks of 15% by mass, were superior facial patches from the viewpoint of having negligible residual adhesive. It was found that the facial patch of Example 4 in which the pressure-sensitive adhesive layer contained this styrene-isoprene-styrene block copolymer, and the support was a low-density polyethylene film having a thickness of 15 μm, was a superior facial patch from the viewpoint of causing less pain at the time of removal and having a smaller area of corneous tissue removal, compared with the facial patch of Example 2 having the same composition for the pressure-sensitive adhesive layer. Furthermore, it was found that the facial patch of Example 1 in which the ratio of the styrene-isoprene-styrene block copolymer and the tackifier resin is 1:2.5, was a particularly excellent facial patch from the viewpoint of having a very small area of corneous tissue removal, such as 12%, compared with the facial patch of Example 6 having the ratio of the block copolymer and the resin of 1:2. Furthermore, when a comparison is made between the facial patch of Example 3 and the facial patch of Example 7, it was found that since the facial patch of Example 3 containing a terpene resin as a tackifier resin has high cohesive force of the pressure-sensitive adhesive, the facial patch of Example 3 has less residual adhesive after removal, and causes less pain at the time of removal.

On the contrary, it was found that the facial patch of Comparative Example 1 in which the content of the softening agent in the pressure-sensitive adhesive layer was a small amount such as 30% by mass, caused pain at the time of removal, and since the facial patch had high adhesive force against a BA-SUS plate and nigh probe tack, the facial patch was highly irritating to the skin. It was found that the facial patch of Comparative Example 2 in which the content of the softening agent in the pressure-sensitive adhesive layer was a large amount such as 70% by mass, had poor attachability to the cheek, and therefore, there was a risk that the facial patch could not be applied over a long period of time onto the skin of the face that overly secretes sebum. Furthermore, it was found that the facial patch of Comparative Example 3 in which the ratio (mass ratio) of the styrene-isoprene-styrene block copolymer and the tackifier resin was 1:1.5, had low adhesive force against a BA-SUS plate and poor attachability to the cheek, and therefore, there was a risk that the facial patch had insufficient adhesive force and could not be applied over a long period of time onto the skin of the face. Furthermore, it was found that the facial patch of Comparative Example 4 in which the support was a polyethylene terephthalate film having a Young's modulus of 4.7 GPa, had poor attachability to the cheek, and there was a risk that the facial patch could not be applied over a long period of time onto the skin of the face that overly secretes sebum.

INDUSTRIAL APPLICABILITY

The present invention can provide a facial patch including a support, a pressure-sensitive adhesive layer, and a release layer in this order, characterized in that:

(a) the pressure-sensitive adhesive layer satisfies the following conditions (a-1) to (a-3);

(a-1) the pressure-sensitive adhesive layer contains a styrene-isoprene-styrene block copolymer, a tackifier resin, and a softening agent;

(a-2) the ratio (mass ratio) of the styrene-isoprene-styrene block copolymer and the tackifier is 1:2 to 1:4; and (a-3) the content of the softening agent is 40% to 60% by mass; and (b) the support has elastic moduli with a Young's modulus of 0.01 GPa to 0.5 GPa, the facial patch being capable of being applied over a long period of time onto the skin of the face that secretes a large amount of sebum, having less residual adhesive, and being less irritating to the skin. Therefore, the present, invention has high industrial applicability.

The invention claimed is:

1. A facial patch comprising a support, a pressure-sensitive adhesive layer, and a release layer, in this order, and, optionally, a carrier film on a surface of the support which is on the opposite side of the pressure-sensitive adhesive layer, wherein the carrier film, when included in the facial patch, is peelable and removed from the support upon application of the facial patch to a facial skin surface, wherein
- (a) the pressure-sensitive adhesive layer satisfies the following conditions (a-1) to (a-3):
- (a-1) the pressure-sensitive adhesive layer consists of a styrene-isoprene-styrene block copolymer, a terpene tackifier resin, and a liquid paraffin softening agent, and, optionally, a drug;
- (a-2) the mass ratio of the styrene-isoprene-styrene block copolymer and the tackifier resin is 1:2 to 1:4; and
- (a-3) the content of the softening agent is 40% to 60% by mass of the pressure-sensitive adhesive layer; and
- (b) the support has elastic moduli with a Young's modulus of 0.01 to 0.5 GPa.

2. The facial patch according to claim 1, wherein the styrene-isoprene-styrene block copolymer includes a styrene-isoprene-styrene block copolymer having a percentage content of styrene of 20% by mass or more.

3. The facial patch according to claim 1, wherein the styrene-isoprene-styrene block copolymer includes a styrene-isoprene-styrene block copolymer having a percentage content of styrene of 15% by mass or more and an amount of diblocks of 30% by mass or less.

4. The facial patch according to claim 1, wherein the pressure-sensitive adhesive layer further satisfies the following conditions (a-2') and (a-3'):
- (a-2') the mass ratio of the styrene-isoprene-styrene block copolymer and the tackifier resin is 1:2.4 to 1:3.5; and
- (a-3') the content of the softening agent is 40% to 55% by mass of the pressure-sensitive adhesive layer.

5. The facial patch according to claim 1, wherein the drug is included in the pressure-sensitive adhesive layer.

6. The facial patch according to claim 1, wherein the support is a polyethylene film having a thickness of 1 μm to 80 μm.

7. The facial patch according to claim 1, comprising the carrier film on the surface of the support, which is on the opposite side of the pressure-sensitive adhesive layer.

8. The facial patch according to claim 7, wherein the carrier film is a polyester film.

9. The facial patch according to claim 7, wherein the carrier film is provided with matt finish on a surface facing the support.

10. A method for producing the facial patch according to claim 1, the method comprising forming the pressure-sensitive adhesive layer on an upper surface of the release layer and laminating the support on a surface of the pressure-sensitive adhesive layer.

11. The facial patch according to claim 8, wherein the carrier film is provided with matt finish on a surface facing the support.

12. The facial patch according to claim 1, wherein the carrier film is included and a surface of the carrier film facing the support has an area that does not cover the support.

13. The facial patch according to claim 1, wherein the pressure-sensitive adhesive layer has a thickness in the range of 1 μm to 50 μm.

* * * * *